(12) United States Patent  
Kozlowski et al.

(10) Patent No.: US 8,304,511 B2  
(45) Date of Patent: **\*Nov. 6, 2012**

(54) MALEAMIC ACID POLYMER DERIVATIVES AND THEIR BIOCONJUGATES

(75) Inventors: Antoni Kozlowski, Huntsville, AL (US); Remy F. Gross, III, Petaluma, CA (US); Samuel P. McManus, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/172,043

(22) Filed: Jun. 29, 2011

(65) Prior Publication Data

US 2011/0262379 A1    Oct. 27, 2011

Related U.S. Application Data

(60) Continuation of application No. 12/642,413, filed on Dec. 18, 2009, now Pat. No. 7,994,272, which is a continuation of application No. 11/904,990, filed on Sep. 27, 2007, now Pat. No. 7,659,361, which is a division of application No. 10/750,996, filed on Dec. 31, 2003, now Pat. No. 7,329,721.

(60) Provisional application No. 60/468,340, filed on May 5, 2003, provisional application No. 60/437,251, filed on Dec. 31, 2002.

(51) Int. Cl.  
*C08G 73/10* (2006.01)  
*C08G 73/00* (2006.01)

(52) U.S. Cl. ........ 528/310; 528/322; 528/363; 525/205; 525/540

(58) Field of Classification Search .................. 528/310, 528/322, 363; 525/205, 540  
See application file for complete search history.

(56) References Cited

U.S. PATENT DOCUMENTS

| | | | |
|---|---|---|---|
| 5,585,484 | A | 12/1996 | Acharya et al. |
| 5,766,897 | A | 6/1998 | Braxton |
| 5,932,462 | A | 8/1999 | Harris et al. |
| 6,017,943 | A | 1/2000 | Acharya et al. |
| 6,180,134 | B1 | 1/2001 | Zalipsky et al. |
| 6,180,598 | B1 | 1/2001 | Nelson |
| 6,183,738 | B1 | 2/2001 | Clark |
| 6,340,742 | B1 | 1/2002 | Burg et al. |
| 6,602,498 | B2 | 8/2003 | Shen |

(Continued)

FOREIGN PATENT DOCUMENTS

EP    0273545    7/1988

(Continued)

OTHER PUBLICATIONS

Cantin, et al., "Polyethylene Glycol Conjugation at Cys232 Prolongs the Half-Life of alpha1 Proteinase inhibitor", Amer. J. of Resp. Cell & Mole, Bio., vol. 27, pp. 659-665, (2002).

(Continued)

*Primary Examiner* — Duc Truong  
(74) *Attorney, Agent, or Firm* — Mark A. Wilson

(57) ABSTRACT

The present invention is directed a method comprising administering a composition to an individual, wherein the composition comprises a plurality of conjugates, each conjugate in the plurality a protein derivatized with a water-soluble polymer, wherein the polymer is coupled to the protein via succinimide groups covalently attached to either cysteine sulfhydryl groups or lysine amino groups, and substantially all of the succinimide groups present in the composition are present in a ring-opened form.

18 Claims, 3 Drawing Sheets

U.S. PATENT DOCUMENTS

| | | | |
|---|---|---|---|
| 6,875,841 | B2 | 4/2005 | Sakanoue et al. |
| 7,329,721 | B2 | 2/2008 | Kozlowski et al. |
| 7,659,361 | B2 | 2/2010 | Kozlowski et al. |
| 2001/0044526 | A1 | 11/2001 | Shen |
| 2003/0065134 | A1 | 4/2003 | Sakanoue et al. |
| 2004/0167287 | A1 | 8/2004 | Kozlowski et al. |
| 2008/0146771 | A1 | 6/2008 | Kozlowski et al. |
| 2010/0113329 | A1 | 5/2010 | Kozlowski et al. |

FOREIGN PATENT DOCUMENTS

| | | |
|---|---|---|
| EP | 0318162 | 5/1989 |
| EP | 0839849 | 5/1998 |
| EP | 1172372 | 1/2002 |
| EP | 1267170 | 12/2002 |
| EP | 1283233 | 2/2003 |
| EP | 1578841 | 6/2008 |
| JP | 2000-191700 | 7/2000 |
| WO | 92/16221 | 10/1992 |
| WO | 93/09143 | 5/1993 |
| WO | 99/03887 | 1/1999 |
| WO | 99/64460 | 12/1999 |
| WO | 00/21594 | 4/2000 |
| WO | 01/62827 | 8/2001 |
| WO | 01/87925 | 11/2001 |

OTHER PUBLICATIONS

Han, et al., "Sugar Transport by the Bacterial Phosphotransferase System", The J. of Bio. Chem., vol. 265, No. 4, pp. 1996-2003, (1990).
Ishii, et al., "Effects of the State of the Succinimido-Ring on the Fluorescene and Structural Properties of Pyrene Maleimide-Labeled alpha alpha-Tropomyosin", Biophys. J., vol. 50, pp. 75-80, (1986).
Kogan, "The Synthesis of Substituted Methoxy-Poly(ethylene glycol) Derivatives Suitable for Selective Protein Modification", Synthetic Comm., vol. 22, No. 16, pp. 2417-2424, (1992).
Manjula, et al., "Cys-93-beta beta-Succinimidophenyl Polyethylene Glycol 2000 Hemoglobin A", The J. of Bio. Chem., vol. 275, No. 8, pp. 5527-5534, (2000).
Roberts, et al., Chemistry for peptide and protein PEGylation, Adv. Drug Del. Rev., vol. 54, pp. 459-476, (2002).
Tsutsumi, et al., "Site-specific chemical modification with polyethylene glycol of recombinant immunotoxin anti-Tac (Fv)-PE38(LMB-2) improves Antitumor activity and reduces animal toxicity and immunogenicity", PNAS, vol. 97, No. 15, pp. 8548-8553, (Jul. 18, 2000).
Veronese, "Peptide and protein PEGylation: a review of problem and solutions", Biomaterials, vol. 22, pp. 405-417, (2001).
Wu, et al., "p53 protein oxidation in cultured cells in response to pyrrolidine dithiocarbamate: a novel method for relating the amount of p53 oxidation in vivo to the regulation of p53-responsive genes", Biochem. J., vol. 351, pp. 87-93, (2000).
Nektar Transforming Therapeutics, Nektar Molecule Engineering Polyethylene Glycol and Derivatives for Advanced PEGylation, pp. 1-20, Catalog—2003, (Jul. 2003).
NOF Corporation, "PEG Derivatives, Phospholipid and Drug Delivery Materials for Pharmaceuticals", pp. 1-46, Catalogue 2003—1st, (Jan. 2003).
NOF Corporation, "PEG Derivatives, Phospholipid and Drug Delivery Materials for Pharmaceuticals", pp. 1-50, Catalogue 2003—2nd, (Mar. 2004).
Shearwater Polymers, Inc., pp. 2-49, (Catalog—Mar. 1995).
Shearwater Polymers, Inc., Polyethylene Glycol and Derivatives, pp. 1-53, (Catalog—Jul. 1997).
Shearwater Polymers, Inc., Polyethylene Glycol and Derivatives: Functionalized Biocompatible Polymers for Research and Pharmaaceuticals, pp. 1-50, (Catalog—2000).
Shearwater Corporation, Polyethylene Glycol and Derivatives for Biomedical Applications, pp. 1-17, (Catalog—2001).
Translations of Notice of Opposition from KNH Patentanwalte to the EPO dated Mar. 25, 2009 against European Patent EP 1578841.
Australian Examiners First Report corresponding to Australian Patent Application No. 2003300139 dated Sep. 19, 2007.
Canadian Office Action corresponding to Canadian Patent Application No. 2,509,260 dated Sep. 16, 2010.
Chinese First Office Action corresponding to Chinese Patent Application No. 200380108082.1 date of notification Jan. 12, 2007.
European Communication corresponding to European Patent Application No. 03 800 397.6 dated Oct. 18, 2005.
European Communication corresponding to European Patent Application No. 03 800 397.6 dated Feb. 20, 2006.
Indian First Examination Report corresponding to Indian Patent Application No. 2712/DELNP/2005 dated Nov. 13, 2007.
Japanese Notice of Reasons for Rejection corresponding to Japanese Patent Application No. 2005-508648 mailing date Jul. 21, 2009.
Korean Notice of Grounds for Rejection corresponding to Korean Patent Application No. 2005-7012473 issued Sep. 14, 2010.
Mexican First Office Action corresponding to Mexican Patent Application No. 2005/007163 dated Jul. 11, 2008.
PCT International Search Report corresponding to PCT/US2003/041705 date of mailing Jul. 14, 2004.
PCT International Preliminary Examination Report corresponding to PCT/US2003/041705 date of mailing Mar. 21, 2005.
Office Action corresponding to Canadian Patent Application No. 2,509,260 dated May 24, 2011.

MALEAMIC ACID POLYMER DERIVATIVES AND THEIR BIOCONJUGATES

CROSS REFERENCE TO RELATED APPLICATIONS

This application is a continuation application of U.S. patent application Ser. No. 12/642,413, filed Dec. 18, 2009, now U.S. Pat. No. 7,994,272, which is a continuation application of U.S. patent application Ser. No. 11/904,990, filed Sep. 27, 2007, now U.S. Pat. No. 7,659,361, which is a divisional application of U.S. patent application Ser. No. 10/750,996, filed Dec. 31, 2003, now U.S. Pat. No. 7,329,721, which claims the benefit of priority to U.S. provisional application Ser. No. 60/468,340, filed May 5, 2003, and to U.S. provisional application Ser. No. 60/437,251, filed Dec. 31, 2002, the disclosures of each of the foregoing are incorporated herein by reference in their entireties.

FIELD OF THE INVENTION

This invention relates generally to the field of polymer chemistry, and more specifically to chemically stable active agent conjugates prepared from maleimide- or maleamic acid functionalized water-soluble polymers such as polyethylene glycol, and to methods for synthesizing, characterizing, and using such polymer reagents and conjugates.

BACKGROUND OF THE INVENTION

Due to recent advances in biotechnology, therapeutic proteins and other biomolecules, e.g. antibodies and antibody fragments, can now be prepared on a large scale, making such biomolecules more widely available. Unfortunately, the clinical usefulness of potential therapeutic biomolecules is often hampered by their rapid proteolytic degradation, low bioavailability, instability upon manufacture, storage or administration, or by their immunogenicity. Due to the continued interest in administering proteins and other biomolecules for therapeutic use, various approaches to overcoming these deficiencies have been explored.

One approach that has been widely explored is the modification of proteins and other potentially therapeutic molecules by covalent attachment of a water-soluble polymer such as polyethylene glycol or "PEG" (Abuchowski, A., et al, J. Biol. Chem. 252 (11), 3579 (1977); Davis, S., et al., Clin. Exp Immunol., 46, 649-652 (1981). The biological properties of PEG-modified proteins, also referred to as PEG-conjugates or pegylated proteins, have been shown, in many cases, to be considerably improved over those of their non-pegylated counterparts (Herman, et al., Macromol. Chem. Phys., 195, 203-209 (1994). Polyethylene glycol-modified proteins have been shown to possess longer circulatory times in the body due to increased resistance to proteolytic degradation, and also to possess increased thermostability (Abuchowski, A., et al., J. Biol. Chem., 252, 3582-3586 (1977). A similar increase in bioefficacy is observed with other biomolecules, e.g. antibodies and antibody fragments (Chapman, A., Adv. Drug Del. Rev. 54, 531-545 (2002)).

Typically, attachment of polyethylene glycol to a drug or other surface is accomplished using an activated PEG derivative, that is to say, a PEG having at least one activated terminus suitable for reaction with a nucleophilic center of a biomolecule (e.g., lysine, cysteine and similar residues of proteins). Most commonly employed are methods based upon the reaction of an activated PEG with protein amino groups, such as those present in the lysine side chains of proteins. Polyethylene glycol having activated end groups suitable for reaction with the amino groups of proteins include PEG-aldehydes (Harris, J. M., Herati, R. S., Polym Prepr. (Am. Chem. Soc., Div. Polym. Chem), 32(1), 154-155 (1991), mixed anhydrides, N-hydroxysuccinimide esters, carbonylimadazolides, and chlorocyanurates (Herman, S., et al., Macromol. Chem. Phys. 195, 203-209 (1994)). Although many proteins have been shown to retain activity during PEG modification, in some instances, polymer attachment through protein amino groups can be undesirable, such as when derivatization of specific lysine residues inactivates the protein (Suzuki, T., et al., Biochimica et Biophysica Acta 788, 248-255 (1984)). Moreover, since most proteins possess several available/accessible amino groups, the polymer conjugates formed are typically mixtures of mono-pegylated, di-pegylated, tri-pegylated species and so on, which can be difficult and also time-consuming to characterize and separate. Further, such mixtures are often not reproducibly prepared, which can create problems during scale-up for regulatory approval and subsequent commercialization.

One method for avoiding these problems is to employ a site-selective polymer reagent that targets functional groups other than amines. One particularly attractive target is the thiol group, which in proteins is present in the amino acid, cysteine. Cysteines are typically less abundant in proteins than lysines, thus reducing the likelihood of protein deactivation upon conjugation to these thiol-containing amino acids. Moreover, conjugation to cysteine sites can often be carried out in a well-defined manner, leading to the formation of single species polymer-conjugates.

Polyethylene glycol derivatives having a thiol-selective reactive end group include maleimides, vinyl sulfones, iodoacetamides, thiols, and disulfides, with maleimides being the most popular. These derivatives have all been used for coupling to the cysteine side chains of proteins (Zalipsky, S. Bioconjug. Chem. 6, 150-165 (1995); Greenwald, R. B. et al. Crit. Rev. Ther. Drug Carrier Syst. 17, 101-161 (2000); Herman, S., et al., Macromol. Chem. Phys. 195, 203-209 (1994)). However, many of these reagents have not been widely exploited due to the difficulty in their synthesis and purification.

Polyethylene glycol derivatives having a terminal maleimide group are one of the most popular types of sulfhydryl-selective reagents, and are commercially available from a number of sources. Although not widely appreciated or recognized, the Applicants have recognized that many PEG-maleimides unfortunately exhibit hydrolytic instability during storage and/or conjugation to a drug candidate. More particularly, a substantial degree of hydrolysis of the maleimide ring has been observed, both prior to and after conjugation. This instability can result in the formation of multiple species of drug conjugates within a drug-conjugate composition. The various drug conjugate species are likely to possess similar biological activities, but may differ in their pharmacokinetic properties. This is particularly disadvantageous for compositions intended for patient administration, since the resulting drug compositions can be ill-defined mixtures of drug conjugate species whose particular safety and accumulation profiles are unknown. Moreover, due to different factors impacting hydrolysis rates, inconsistency between drug conjugate batch compositions can present an additional problem.

Another problem has been observed by the applicants is the de-pegylation of conjugates prepared from PEG maleimides to yield mixtures of altered drug and detached PEG impurity. For these reasons, the Applicants have found that PEG maleimides can be undesirable reagents for coupling to thiol groups on target drugs or other active agents. Previous attempts to address this problem have focused on increasing the stability of a polymer maleimide by making it less prone to hydrolysis (i.e., ring-opening). See for example, U.S. Patent Application Publication No. US 2003/0065134.

Thus, the applicants have realized a continuing need in the art for the development of new activated PEGs useful for coupling to biologically active molecules, desirably in a site-selective fashion, that overcome the shortcomings of presently-available thiol-selective polymer reagents and are stable during both storage and coupling. This invention meets those needs.

SUMMARY OF THE INVENTION

The present invention provides thiol-selective polymer reagents and their conjugates that (i) are stable during storage and coupling, (ii) are resistant to hydrolysis, and (iii) exhibit increased resistance to de-pegylation, thereby allowing formation of substantially chemically stable and well-defined drug conjugate compositions to be described in greater detail below.

The present invention is based upon the Applicants' recognition of the need for an alternative to conventional polymer maleimide reagents. In response to this need, the Applicants have devised an approach that is completely contrary to other approaches employed to date. That is to say, rather than utilizing a customary approach and attempting to prevent hydrolysis of the maleimide ring, the Applicants have instead intentionally forced open the maleimide ring, to provide polymer reagents and conjugates where the "maleimide" is converted to its stable succinamic acid opened-ring form.

More particularly, in one aspect, provided herein is a method wherein a maleimide group of a water-soluble polymer is forcibly (intentionally) converted to its ring-open maleamic acid form, either prior to or more conventionally after coupling to an active agent. In this way, a maleamic acid or succinamic acid polymer composition is provided that possesses: (i) well-defined components, and (ii) a diminished tendency towards hydrolysis, particularly in comparison to its maleimide-derived, succinimide counterparts.

More specifically, in one aspect, the invention provides a method for preparing a polymer conjugate. The method includes the steps of (a) providing a water-soluble polymer comprising a maleimide group, and (b) reacting the polymer with an active agent that possesses a nucleophile under conditions effective to couple the active agent to the water soluble polymer via a Michael-type addition reaction to form a polymer-succinimide-linked active agent conjugate. This conjugate, in step (c), is then treated under conditions effective to force open the succinimide ring, to form a polymer-succinamic acid-conjugate.

In one embodiment, the maleimide ring is forced open via a hydrolysis reaction. Typically, the ring-opening hydrolysis is carried out in the presence of a base that can be in solution or on a solid support. Typical pHs for conducting the hydrolysis are in a range of about 6 to 12.

In a preferred embodiment, the hydrolysis is carried out under conditions effective to provide a chemically stable polymer-succinamic acid-conjugate composition.

In one embodiment of the method, the hydrolysis reaction is carried out until at least about 15% of the polymer succinamic acid conjugate is formed, based upon the conversion of the closed ring-form. In alternative embodiments, the hydrolysis reaction is carried out until at least about 35%, or 50%, or 80%, or 95%, or 98% or essentially 100% polymer succinamic acid conjugate is formed, i.e., where the polymer maleimide conjugate is essentially fully ring-opened.

Water soluble polymers for use in the invention include poly(alkylene oxide), poly(vinyl pyrrolidone), poly(vinyl alcohol), polyoxazoline, poly(acryloylmorpholine), and poly (oxyethylated polyol). A preferred water-soluble polymer is polyethylene glycol.

In yet another aspect, provided herein is a polymer succinamic acid conjugate composition prepared by the method described above.

In yet another aspect, provided herein is a composition that comprises:

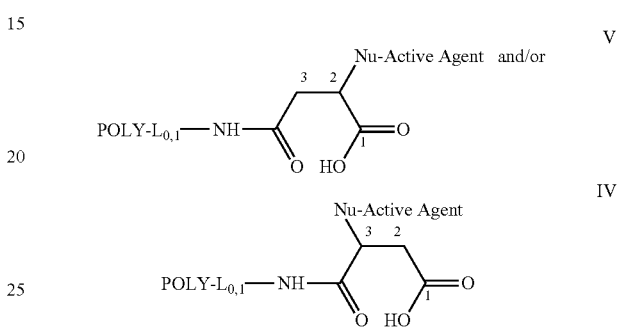

where POLY is a water-soluble polymer segment, L is an optional linker, and "Nu-Active agent" represents an active agent comprising a nucleophile, "Nu". Preferred nucleophiles include thiol, thiolate, and amino.

In yet another aspect, the invention provides a protein derivatized with a water-soluble polymer, where the polymer is coupled to the protein via succinimide groups covalently attached to either cysteine sulfyhydryl groups or lysine amino groups, and substantially all of the succinimide groups are present in a ring-opened form.

These and other objects and features of the invention will become more fully apparent when read in conjunction with the following figures and detailed description.

DETAILED DESCRIPTION OF THE INVENTION

Figure 1:
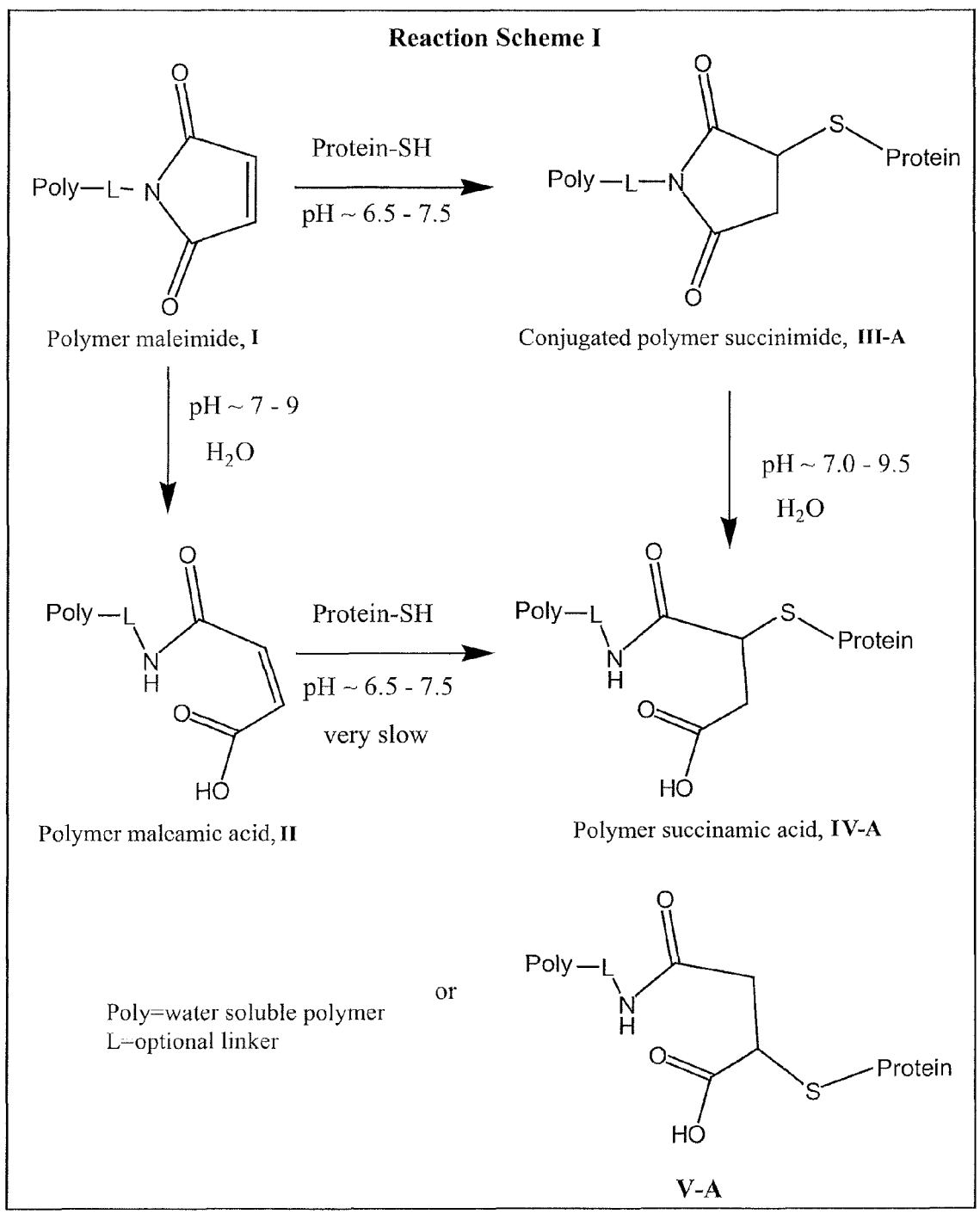
FIG. 1 illustrates an exemplary reaction of both a polymer maleimide and a polymer maleamic acid with a thiol group of a representative active agent, in this case, a protein, to form a polymer-succinamic acid conjugate of the invention.

Before describing the present invention in detail, it is to be understood that this invention is not limited to the particular polymers, synthetic techniques, active agents, and the like as such may vary. It is also to be understood that the terminology used herein is for describing particular embodiments only, and is not intended to be limiting.

In describing and claiming the present invention, the following terminology will be used in accordance with the definitions described below.

DEFINITIONS

The following terms as used herein have the meanings indicated.

As used in the specification, and in the appended claims, the singular forms "a", "an", "the", include plural referents unless the context clearly dictates otherwise.

"PEG" or "poly(ethylene glycol)" as used herein, is meant to encompass any water-soluble poly(ethylene oxide). Typically, PEGs for use in the present invention will comprise one of the two following structures: "—(CH$_2$CH$_2$O)$_n$—" or "—(CH$_2$CH$_2$O)$_{n-1}$CH$_2$—," depending upon whether or not the terminal oxygen(s) has been displaced, e.g., during a synthetic transformation. The variable (n) ranges from 3 to 3000, and the terminal groups and architecture of the overall PEG may vary. When PEG further comprises a linker moiety (to be described in greater detail below), the atoms comprising the linker, when covalently attached to a PEG segment, do not result in formation of (i) an oxygen-oxygen bond (—O—O—, a peroxide linkage), or (ii) a nitrogen-oxygen bond (N—O, O—N). "PEG" means a polymer that contains a majority, that is to say, greater than 50%, of subunits that are —CH$_2$CH$_2$O—. PEGs for use in the invention include PEGs having a variety of molecular weights, structures or geometries (e.g., branched, linear, forked PEGs, dendritic, and the like), to be described in greater detail below.

"PEG diol", also known as alpha-,omega-dihydroxylpoly(ethylene glycol), can be represented in brief form as HO-PEG-OH, where PEG is as defined above.

"Water-soluble", in the context of a polymer of the invention or a "water-soluble polymer segment" is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

An "end-capping" or "end-capped" group is an inert or non-reactive group present on a terminus of a polymer such as PEG. An end-capping group is one that does not readily undergo chemical transformation under typical synthetic reaction conditions. An end capping group is generally an alkoxy group, —OR, where R is an organic radical comprised of 1-20 carbons and is preferably lower alkyl (e.g., methyl, ethyl) or benzyl. "R" may be saturated or unsaturated, and includes aryl, heteroaryl, cyclo, heterocyclo, and substituted forms of any of the foregoing. For instance, an end capped PEG will typically comprise the structure "RO—(CH$_2$CH$_2$O)$_n$—", where R is as defined above. Alternatively, the end-capping group can also advantageously comprise a detectable label. When the polymer has an end-capping group comprising a detectable label, the amount or location of the polymer and/or the moiety (e.g., active agent) to which the polymer is coupled, can be determined by using a suitable detector. Such labels include, without limitation, fluorescers, chemiluminescers, moieties used in enzyme labeling, colorimetric (e.g., dyes), metal ions, radioactive moieties, and the like. The end-capping group can also advantageously comprise a phospholipid. When the polymer has an end-capping group such as a phospholipid, unique properties (such as the ability to form organized structures with similarly end-capped polymers) are imparted to the polymer. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer of the invention means a polymer that in its entirety is not found in nature. A non-naturally occurring polymer of the invention may however contain one or more subunits or segments of subunits that are naturally occurring, so long as the overall polymer structure is not found in nature.

"Molecular mass" in the context of a water-soluble polymer of the invention such as PEG, refers to the nominal average molecular mass of a polymer, typically determined by size exclusion chromatography, light scattering techniques, or intrinsic velocity determination in 1,2,4-trichlorobenzene. The polymers of the invention are typically polydisperse, possessing low polydispersity values of less than about 1.20.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive" or "inert" with reference to a functional group present on a molecule in a reaction mixture, indicates that the group remains largely intact under conditions effective to produce a desired reaction in the reaction mixture.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof is meant to encompass protected forms thereof.

The term "linker" is used herein to refer to an atom or a collection of atoms optionally used to link interconnecting moieties, such as a polymer segment and a maleimide. The linkers of the invention are generally hydrolytically stable.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides, thioesters, thiolesters, and carbonates.

An "enzymatically degradable linkage" means a linkage that is subject to degradation by one or more enzymes.

A "hydrolytically stable" linkage or linker, for the purposes of the present invention, and in particular in reference to the polymers of the invention, refers to an atom or to a collection of atoms, that is hydrolytically stable under normal physiological conditions. That is to say, a hydrolytically stable linkage does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Hydrolysis rates of representative chemical bonds can be found in most standard chemistry textbooks.

"Branched" in reference to the geometry or overall structure of a polymer refers to polymer having 2 or more polymer "arms". A branched polymer may possess 2 polymer arms, 3 polymer arms, 4 polymer arms, 6 polymer arms, 8 polymer arms or more. One particular type of highly branched polymer is a dendritic polymer or dendrimer, that for the purposes of the invention, is considered to possess a structure distinct from that of a branched polymer.

"Branch point" refers to a bifurcation point comprising one or more atoms at which a polymer splits or branches from a linear structure into one or more additional polymer arms.

A "dendrimer" is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

"Substantially" or "essentially" means nearly totally or completely, for instance, 95% or greater of some given quantity.

An "alkyl" or "alkylene" group, depending upon its position in a molecule and the number of points of attachment of the group to atoms other than hydrogen, refers to a hydrocarbon chain or moiety, typically ranging from about 1 to 20 atoms in length. Such hydrocarbon chains are preferably but not necessarily saturated unless so indicated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like.

"Lower alkyl" or "lower alkylene" refers to an alkyl or alkylene group as defined above containing from 1 to 6 carbon atoms, and may be straight chain or branched, as exemplified by methyl, ethyl, n-butyl, i-butyl, t-butyl.

"Cycloalkyl" or "cycloalkylene", depending upon its position in a molecule and the number of points of attachment to atoms other than hydrogen, refers to a saturated or unsaturated cyclic hydrocarbon chain, including polycyclics such as bridged, fused, or Spiro cyclic compounds, preferably made up of 3 to about 12 carbon atoms, more preferably 3 to about 8.

"Lower cycloalkyl" or "lower cycloalkylene" refers to a cycloalkyl group containing from 1 to 6 carbon atoms.

"Alicyclic" refers to any aliphatic compound that contains a ring of carbon atoms. An alicyclic group is one that contains a "cycloalkyl" or "cycloalkylene" group as defined above that is substituted with one or more alkyl or alkylenes.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methyl, ethyl, propyl, benzyl, etc.), preferably $C_1$-$C_7$.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-propynyl, isopropynyl, n-butynyl, isobutynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion, atom, or collection of atoms that may be ionic, having an electrophilic center, i.e., a center that is electron seeking, capable of reacting with a nucleophile.

"Nucleophile" refers to an ion or atom or collection of atoms that may be ionic, having a nucleophilic center, i.e., a center that is seeking an electrophilic center, and capable of reacting with an electrophile.

"Active agent" as used herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a PEG-active agent conjugate present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

"Multi-functional" in the context of a polymer of the invention means a polymer backbone having 3 or more functional groups contained therein, where the functional groups may be the same or different, and are typically present on the polymer termini. Multi-functional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

A "difunctional" polymer means a polymer having two functional groups contained therein, typically at the polymer termini. When the functional groups are the same, the polymer is said to be homodifunctional. When the functional groups are different, the polymer is said to be heterobifunctional A basic or acidic reactant described herein includes neutral, charged, and any corresponding salt forms thereof.

"Polyolefinic alcohol" refers to a polymer comprising an olefin polymer backbone, such as polyethylene, having multiple pendant hydroxyl groups attached to the polymer backbone. An exemplary polyolefinic alcohol is polyvinyl alcohol.

As used herein, "non-peptidic" refers to a polymer backbone substantially free of peptide linkages. However, the polymer may include a minor number of peptide linkages spaced along the repeat monomer subunits, such as, for example, no more than about 1 peptide linkage per about 50 monomer units.

The term "patient," refers to a living organism suffering from or prone to a condition that can be prevented or treated by administration of a polymer of the invention, typically but not necessarily in the form of a polymer-active agent conjugate, and includes both humans and animals.

"Optional" or "optionally" means that the subsequently described circumstance may or may not occur, so that the description includes instances where the circumstance occurs and instances where it does not.

By "residue" is meant the portion of a molecule remaining after reaction with one or more molecules. For example, a biologically active molecule residue in a polymer conjugate of the invention typically corresponds to the portion of the biologically active molecule up to but excluding the covalent linkage resulting from reaction of a reactive group on the biologically active molecule with a reactive group on a polymer reagent.

The term "conjugate" is intended to refer to the entity formed as a result of covalent attachment of a molecule, e.g., a biologically active molecule or any reactive surface, to a reactive polymer molecule, preferably a reactive poly(ethylene glycol).

The term "electron withdrawing group" refers to a chemical moiety that brings electron density towards itself and away from other areas of a molecule through either mesomeric mechanisms (i.e., adding or removing local electron density through $\pi$ bonds) or inductive mechanisms (i.e., an electronegative moiety withdrawing electron density along a $\sigma$ bond, thereby polarizing the bond).

"Chemically stable" in the context of the compositions, polymers and conjugates described herein, refers to a sample that undergoes a 5% or less change in its polymer composition (that is to say, the subject polymer, conjugate or the like is not chemically altered or degraded in any significant manner, for example, where applicable, by de-pegylation or hydrolysis to result in chemical species that are different in amounts or in their structure from those originally present in the sample) over a 3 month time period when measured from the time of initial sample preparation and stored as a buffered solution at substantially neutral pHs (e.g., 6.8 to 7.2) under ambient conditions.

A polymer or composition that is "resistant to hydrolysis", in the context of the present invention, is one that undergoes hydrolysis to an extent less than 5%, when stored over a 3 month time period when measured from the time of initial sample preparation, and stored as a buffered solution at substantially neutral pHs (e.g., 6.8 to 7.2) under ambient conditions.

A "2 or 3-substituted succinamic acid" refers to the position of a substituent, e.g., a nucleophile that is part of an active agent on a polymer succinamic acid, where the carboxylic acid group of the succinamic acid represents carbon number 1, and the carbon or position adjacent to that is carbon number 2, and so on.

OVERVIEW OF THE INVENTION

Customarily, maleimide groups positioned on a polymer are used to covalently attach or conjugate a polymer to an active agent such as a biomolecule, especially a biomolecule containing one or more reactive thiol groups. Such thiol groups may be naturally occurring, or alternatively, the biomolecule may be modified or engineered to contain a thiol suitable for coupling to a maleimide. Under certain more rigorous reaction conditions, e.g., at higher pH levels, active amino groups on a biomolecule can also add to a maleimide group on a polymer derivative to form the corresponding conjugate. Through a series of experiments, the Applicants have recognized that certain polymer-maleimide derivatives, depending upon their structure, are prone towards hydrolysis to form the ring-opened maleamic acid form of the polymer, either before or after conjugation to an active agent. The hydrolysis reaction is not only dependent upon the overall structure of the polymer derivative, but is also pH dependent. Generally, the rate of hydrolysis increases with increasing pH. Additionally, depending upon the moisture content and pH of the resulting composition, formation of the ring-open form of the polymer conjugate can also occur upon storage of a dry polymer conjugate composition, e.g., one where the active agent is a non-protein drug. In cases where ring opening occurs, the resulting composition may actually be a complicated mixture of ring-open and ring-closed conjugates. In general, such hydrolysis can be problematic, particularly for commercial pharmaceutical compositions where long-term stability and consistency in drug lots are highly desirable features.

In an effort to address this problem, the invention provides certain maleamic acid polymer derivatives, their conjugates, and compositions containing them, along with methods for making and using such maleamic acid-derived polymer derivatives. The polymers of the invention are provided to overcome the problems associated with maleimide-functionalized polymers by forcing or promoting the hydrolysis of the maleimide ring, either before or more preferably subsequent to conjugation. In this way, ring-open polymer maleamic acid structures are provided which are much more stable than their maleimide (or succinimide) counterparts. Preferably, the polymer maleamic acid compositions of the invention possess well-defined and substantially unchanging amounts of polymer maleamic acid or polymer succinamic acid conjugates, such that the compositions of the invention are particularly well-suited for use as pharmaceutical compositions for administration to mammalian subjects.

Figure 2:
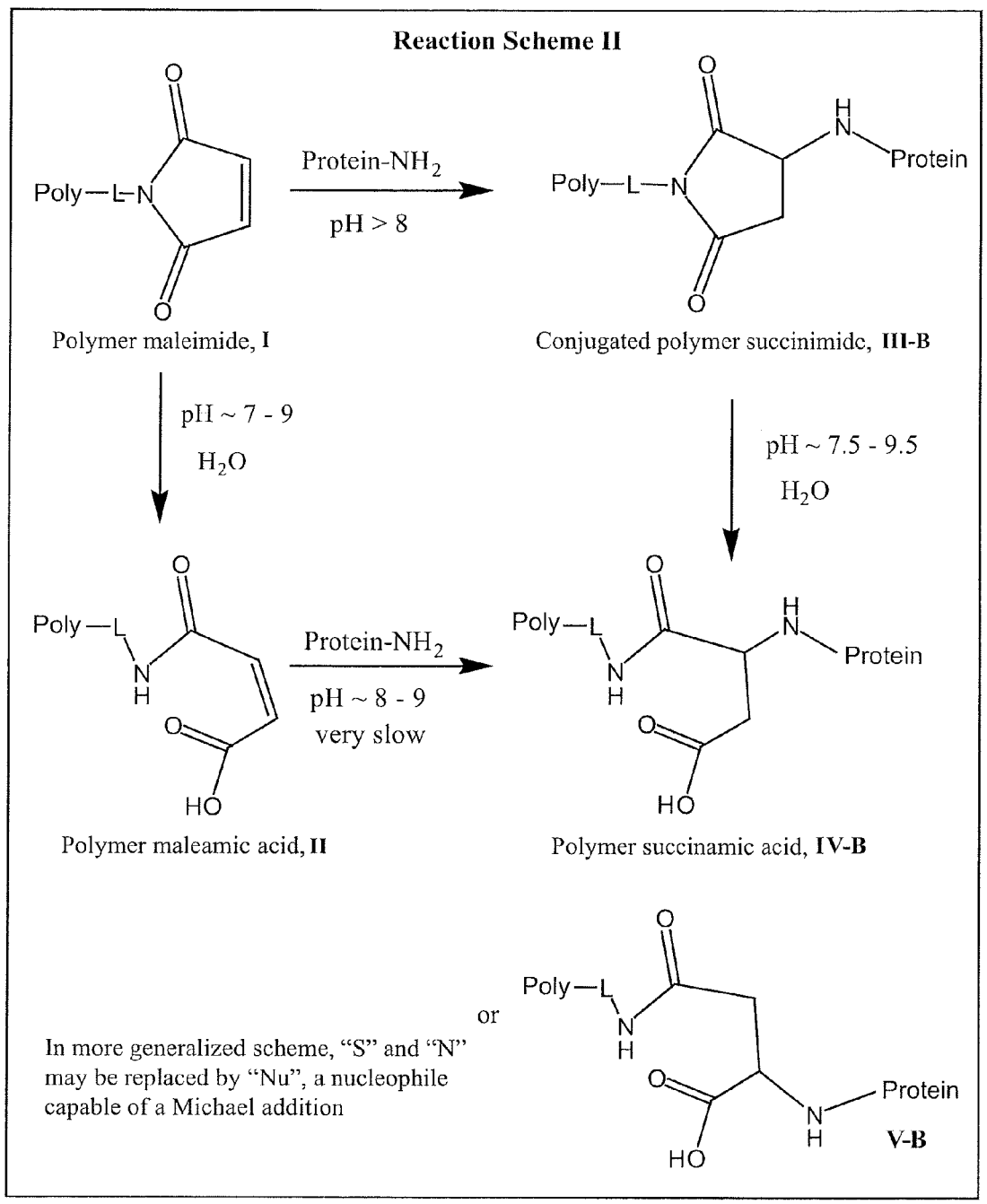
FIG. 2 illustrates an exemplary reaction of both a polymer maleimide and a polymer maleamic acid with an amino group of a representative active agent, in this case, a protein, to form a polymer-succinamic acid conjugate of the invention.

Two illustrative reaction schemes demonstrating an overview of this approach are provided herein as FIG. 1 and FIG. 2. Reaction Scheme I (FIG. 1) illustrates the reaction of both a polymer-maleimide (structure I) and a polymer maleamic acid (structure II) with a thiol-group of a biologically active molecule, in this case, a protein. The reaction conditions shown in FIGS. 1 and 2 are meant to be exemplary only and are not meant to be limiting. Reaction Scheme II (FIG. 2) similarly illustrates reaction of both a polymer-maleimide and a polymer maleamic acid with an amino-group of a biologically active molecule, in this case, a protein. In each scheme, both of the isomeric structures of the conjugated succinamic acid products are shown (structures IV and V, where IV-A and V-A correspond to the thiol-conjugated polymer succinamic acid and IV-B and V-B correspond to the amino-conjugated polymer succinamic acid. The two different products arise from addition of the incoming nucleophile to either of the two carbons, C-2 or C-3, of the double bond of the maleimide ring.

In looking at either FIG. 1 or FIG. 2, it can be seen that while conjugation of an active agent to a polymer maleamic acid, II, can be carried out, the reaction is particularly slow. For this reason, a more preferred route to the desired succinamic acid conjugate is by hydrolysis of the polymer succinimide conjugate, shown generally as structure III. That is to say, in comparison to the corresponding polymer maleimide derivatives, maleamic acid polymer derivatives are less reactive with nucleophiles to form the corresponding conjugates. Thus, conjugation to a polymer maleimide followed by ring opening is generally preferred over ring-opening of a polymer maleimide followed by conjugation, although both approaches result in formation of polymer-succinamic acid conjugates, shown generally as structures IV and V.

Formation of Maleamic and succinamic Acid Polymer Derivatives and Conjugates

Polymer Maleimdies.

In general, the methods provided herein begin with a polymer maleimide. Polymer maleimides can be obtained from commercial sources, such as from Nektar, Huntsville, Ala. For instance, polymer maleimides such as mPEG(MAL)2, mPEG2(MAL)2, mPEG2-MAL, and mPEG-MAL are commercially available from Nektar in a wide range of molecular weights. Structures corresponding to these polymer maleimides are found in the Nektar Catalog, 2001, entitled, "Polyethylene Glycol and Derivatives for Biomedical Applications", on page 8, and are incorporated herein by reference.

Alternatively, the polymer maleimides of the invention can be prepared by any of a number of synthetic routes including the following. In one approach, a maleimide-terminated polymer is prepared by reacting a functional group attached to a polymer segment (i.e., an activated polymer segment) with a functional group of a bifunctional reagent having as one of its functional groups either a maleimide or a functional group that can be converted to a maleimide, such as an amino group. Reacting the polymer segment with a bifunctional reagent results in covalent attachment, typically through a hydrolytically stable linkage, of the reagent to the polymer segment to provide either a polymer maleimide or a polymer maleimide precursor.

For example, the bifunctional reagent may possess the structure A-L-B, wherein A is a first functional group that is reactive with a second functional group on the polymer segment to form a linkage, L, to form POLY-L-B, where B is a maleimide or a functional group that can be readily converted to a maleimide (e.g., an amine that can be converted to a maleimide by reaction with methoxycarbonylmaleimide). In the above approach, A can be any of a number of functional groups such as halo, hydroxyl, active ester such as N-succinimidyl ester, active carbonate, acetal, aldehyde, aldehyde hydrate, alkenyl, acrylate, methacrylate, acrylamide, active sulfone, thiol, carboxylic acid, isocyanate, isothiocyanate, maleimide, vinylsulfone, dithiopyridine, vinylpyridine, iodoacetamide, and epoxide, suitable for reacting with the target group on the activated polymer reagent.

In instances where an approach is employed that utilizes a polymer amine, POLY-$L_{0,1}$-$NH_2$ as a starting material or intermediate, the amine can be transformed into a maleimide, for example, using maleic anhydride. Preferably, the polymer amine is purified prior to conversion to a maleimide group, for example, by chromatography or any other suitable method, to improve the purity of the final maleimide product. In one particular approach, a polymer amine is first reacted with maleic anhydride to form an open ring amide carboxylic acid intermediate, which is then closed in a second step by heating the intermediate in the presence of acetic anhydride and a salt of acetic acid, such as sodium or potassium acetate. Preferably, the intermediate is heated at a temperature ranging from about 50° C. to about 140° C. for about 0.2 to about 5 hours.

Alternatively, an amino group on POLY-$L_{0,1}$-$NH_2$ can be transformed into a maleimide by reaction with a reagent such as N-methoxycarbonylmaleimide or exo-7-oxa[2.2.1]bicycloheptane-2,3-dicarboxylic anhydride.

Structures corresponding to representative polymer maleamic acids and polymer succinamic acid conjugates (provided in the sections that follow) can be extended to the corresponding starting materials and intermediates as described above.

Conjugation to an Active Agent

A polymer maleimide is coupled to a biologically active molecule or active agent using suitable reaction conditions known in the art. Precise conditions will of course vary depending upon the particular active agent, the precise nucleophile that is to undergo a Michael type addition to the maleimide group, the polymer reagent itself and the like.

Suitable conjugation conditions are those conditions of time, temperature, pH, reagent concentration, solvent, and the like sufficient to effect conjugation between a polymer maleimide and an active agent. The specific conditions depend upon, among other things, the active agent, the type of conjugation desired, the presence of other materials in the reaction mixture and so forth. Sufficient conditions for effecting conjugation in any particular case can be determined by one of ordinary skill in the art upon a reading of the disclosure herein, reference to the relevant literature, and/or through routine experimentation.

Exemplary conjugation conditions include carrying out the conjugation reaction at a pH of from about 6 to about 10, and at, for example, a pH of about 6.0, 6.5, 7.0, 7.5, 8.0, 8.5, 9.0, 9.5, or 10. More preferably, a polymer maleimide is typically conjugated to a sulfhydryl-containing active agent at pHs ranging from about 6-9.5, more preferably at pHs from about 7-9, and even more preferably at pHs from about 7 to 8. Most preferably, thiol-selective conjugation is conducted at pHs around 7.

Reaction temperatures are highly dependent on the reactivity of the biomolecule and can typically range from 0° C. to 75° C., preferably from 10° C. to 45° C., and more preferably from 18° C. to 28° C. Higher temperatures may deactivate the more sensitive biomolecules but may be necessary to convert the more resistant ones.

Conjugation reactions can be carried out in a buffer such as a phosphate or acetate buffer or similar system.

Generally, a slight molar excess of polymer maleimide is employed, for example, a 1.5 to 15-fold molar excess, preferably a 2-fold to 10 fold molar excess. The molar ratio of precursor polymer to biologically active molecule can range from 1.0 to 50, preferably from 1.0 to 8.0, and more preferably from 1.04 to 1.5. Exemplary ratios of polymer reagent to active agent include molar ratios of about 1:1 (polymer reagent:active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time. Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete.

Again, reaction time is a function of the reactivity of the particular active agent and becomes longer when the active agent is both slow to react and sensitive to temperature. In such cases, longer reaction times accompanied by moderate reaction temperatures may be required. Typical reaction times can range from five minutes to 10 days, preferably from 30 minutes to 48 hours, and more preferably from 2 to 17 hours, again dependent upon the reactivity of the components, as typically determined by small scale trial reactions. Agitation (e.g., stirring, shaking, etc.) can optionally be used to facilitate the coupling reaction. For sterically hindered sulfhydryl groups, required reaction times may be significantly longer.

Reactions with amino groups proceed at higher pHs, but are relatively slow in comparison to the reaction with thiol groups.

Particular reaction conditions and methodology should be such that the active molecule retains at least partial activity.

Conjugates thus prepared can then be further characterized using analytical methods such as MALDI, capillary electrophoresis, gel electrophoresis, and/or chromatography. Polymer conjugates resulting from a Michael type addition of an active agent to a polymer maleimide are referred to herein as polymer succinimide conjugates or conjugated polymer succinimides (e.g., see structure III).

Maleimide Ring Hydrolysis.

Having a polymer maleimide or a conjugated polymer succinimide in hand (corresponding to structures I and III, respectively), the polymer species is then hydrolyzed to its open ring form. When starting with a polymer maleimide, the corresponding opened-ring form is referred to herein as a polymer maleamic acid, corresponding to structure II. When derived from a conjugated polymer succinimide (III), the corresponding opened-ring form is referred to herein as a conjugated polymer succinamic acid, corresponding to structure IV or structure V. Structures IV and V are structural isomers, differing only in the point of attachment of the nucleophilic group of the active agent. An incoming nucleophile undergoing a Michael type addition reaction to the maleimide can add either at position C2, relative to the final carboxyl carbon of the opened ring form designated as C1, or at position C3.

Generally, a conjugated succinamic acid is prepared by exposing a polymer maleimide, preferably conjugated to an active agent, to aqueous base under conditions effective to hydrolyze the maleimide group of the polymer to a measurable degree. Preferably, the hydrolysis reaction is carried out by adjusting the reaction conditions (amount of water, temperature, relative molar ratios of reactants, etc.) to achieve a desirable extent of hydrolysis or ring opening. Typically, the hydrolysis reaction is carried out to form at least about 15% or greater of the polymer open-ring form, either conjugated or non-conjugated, relative to its closed-ring polymer counterpart. In focusing now on the polymer succinamic acid conjugates, particularly preferred compositions of the invention contain at least about 35%, preferably 40%, 45%, 50%, 55% 60%, 65%, 70%, 75%, 80%, 85%, 90%, 95%, 99%, or essentially 100% conjugated polymer succinamic acid relative to its unhydrolyzed polymer counterpart. For instance, a hydrolyzed polymer composition that comprises 60% polymer succinamic acid conjugate will therefore contain 40% conjugated polymer succinimide (its closed ring polymer counterpart).

Most preferably, hydrolysis is carried out until complete, that is to say, until essentially all of the polymer maleimide or succinimide groups in the conjugate are converted to their ring-open form and the resulting composition is essentially absent any detectable amounts of the closed ring form. Polymer conjugates that are fully ring opened are the most preferred, since their tendency to undergo the reverse reaction, i.e., a dehydrolysis reaction, is minimal under the hydrolysis conditions employed for the forward, ring-opening reaction. Relative to the partially ring-opened compositions described above, compositions that are fully ring-opened are the most stable towards further chemical transformations such as depegylation or hydrolysis.

Particularly preferred compositions are those containing less than about 50% by weight of the closed ring form, or less than about 40% of the closed ring form. More preferred are compositions having less than about 30%, or more preferably less than about 15% of the closed ring form. Even more preferred are compositions containing less than about 10% by weight, or less than about 5% by weight, or even 2% or less of the closed ring form.

Turning now to the conditions employed for effecting hydrolysis, hydrolysis is generally conducted under basic conditions. By raising the pH of the reaction mixture or solution above neutral pHs, the ring opening reaction can essentially be forced to completion. To achieve the most efficient (i.e., shortest) reaction times, it is desirable to conduct the hydrolysis at the highest pH possible, e.g., up to about 12, to achieve ring-opening while not adversely impacting the activity or integrity of the active agent.

Base-promoted ring opening can be carried out using a basic solution or a base bonded to a solid support material, i.e., an ion exchanger. Preferred bases are those that provide the proper pH for a reasonably rapid ring opening without incurring undesirable side reactions. Exemplary bases include alkali metals such as sodium or potassium metal; alkali metal hydroxides such as lithium hydroxide, sodium hydroxide, potassium hydroxide, and the like, and quaternary ammonium hydroxides such as tetraammonium hydroxide, tetrabutylammonium hydroxide, and benzyltrimethylammonium hydroxide, The hydrolysis is typically carried out at pHs ranging from about 6 to about 12. That is to say, the hydrolysis is conducted at a pH selected from about: 6.0, 6.5, 7.0, 7.5, 8.0, 8.5, 9.0, 9.5, 10.0, 10.5, 11.0, 11.5, or even 12.0. Preferred pHs range from about 7.5 to 11.

The hydrolysis reaction may optionally include a buffer. Exemplary buffers include organic buffers such as HEPES, i.e. 4-(2-hydroxyethyl)-1-piperzineethanesulfonic acid; as well as buffers such as sodium, potassium, or ammonium salts of anions such as citrate, alkylsulfonates, hydroxide, acetate, carbonate, tetraborate, bicarbonate, phosphate, and hydrogen phosphate. Ideally, one should, on a small scale, evaluate the particular base and optional buffer system with the particular maleimide or maleimide conjugate prior to carrying out a large process to make certain that the rate of conversion is acceptable and that there are no undesirable side reactions.

Suitable temperatures for effecting hydrolysis range from about 4° C. to about 75° C., preferably from about 0° C. to about 60° C., more preferably from about 15° C. to about 45° C., and more preferably from about 18° C. to about 30° C. As previously mentioned, reaction times are pH dependent. Reaction times will typically range from about 5 min to several days, e.g., 96 hours or more, if no side reactions are evident. However, preferred times are from about 30 min to about 24 hrs, and more preferably from about 2 hr to about 17 hr. Agitation can optionally be used to facilitate the reaction.

In certain instances, e.g., in the presence of some buffers at certain concentrations of buffer and polymer maleimide, the ring opening reactions can slow down with time. To attain a stable reaction rate, it may be desirable to use a buffer system that provides a stable pH over time under the hydrolysis conditions employed, or alternatively, the pH may be monitored and base added periodically, if necessary, to maintain a constant pH range. It should be emphasized, however, that a constant pH is not required to obtain complete ring opening.

Ideally, the polymer succinimide conjugate is exposed to a base at a sufficient temperature and for a sufficient period of time such that a desired degree of ring opening is achieved. Since the ring-opening reaction can occur over a range of pH values, it is preferable to try to balance achieving short reaction times, e.g., at the higher pHs, and to favor a greater extent of hydrolysis, e.g., to form a fully hydrolyzed composition where essentially all of the succinimide rings are hydrolyzed, against the possibility of the occurrence of competitive side reactions that could lead to undesirable mixtures of products or deactivated active agent. Therefore, through small scale trial reactions, one should ideally choose pH values that minimize such undesired side reactions. For instance, at pH values between 5.0 and 6.5, side reactions are minimal but ring opening of either the polymeric maleimides or their conjugates is very slow, often to a prohibitive degree.

For example, mPEG2-MAL-40K, Structure VII,

Again, it should be understood that if the polymer derivative is intended for conjugation to a biologically active molecule, the hydrolysis reaction conditions and methodology should be such that the biologically active molecule retains at least partial activity.

Following hydrolysis, the pH of polymer succinamic acid conjugate-containing reaction mixture is typically adjusted to pHs from about 5.5 to 8. The composition is then optionally desalted and dried, for example, by lyophilization. The resulting composition can then be further purified, is desired, for example by precipitation or chromatography. Different chromatographic separation approaches that can be utilized include SDS PAGE, gel permeation chromatography, and ion exchange chromatography. One particularly preferred approach is ion exchange chromatography, which is advantageous in separating the polymer succinamic acid conjugate, having a carboxylic acid functionality, from the corresponding closed ring conjugated polymer succinimide. Lowering of the pH and drying of the composition, e.g., by lyophilization, is particularly advantageous for compositions where the extent of ring opening is not complete, that is to say, where hydrolysis has not yet gone to completion, since lower pHs and the absence of water disfavor further hydrolysis. In this way, the composition of the reaction mixture is essentially "frozen", i.e., is chemically stable, at a certain non-equilibrium amount of ring-open form.

Moreover, compositions containing the polymer succinamic acid conjugates described herein may also be further purified to obtain/isolate different PEGylated succinamic acid species. Alternatively, and more preferably for lower molecular weight PEGs, e.g., having molecular weights less than about 20 kilodaltons, preferably less than or equal to about 10 kilodaltons, a product mixture can be purified to obtain a distribution around a certain number of PEGs per protein molecule, where applicable. For example, a product mixture can be purified to obtain an average of anywhere from one to five PEGs per protein, typically an average of about 3 PEGs per protein. The strategy for purification of the final conjugate reaction mixture will depend upon a number of factors—the molecular weight of the polymer employed, the particular protein, the desired dosing regimen, and the residual activity and in vivo properties of the individual conjugate(s) species. This approach is more generally applicable to conjugates prepared by reaction of a PEG maleimide with protein amino groups that typically are present in a greater abundance within a given protein than are sulhydryl groups.

If desired, PEG conjugates having different molecular weights can be isolated using gel filtration chromatography.

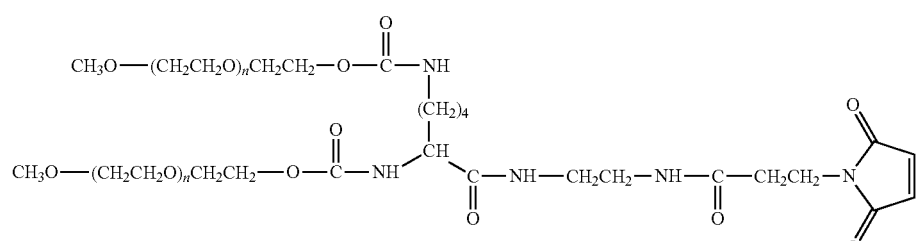

VII obtainable from Nektar (Huntsville, Ala.), undergoes a very limited degree of hydrolysis of the maleimide ring under certain conditions to form the corresponding maleamic acid. Data corresponding to the kinetics of the ring opening reaction is provided in Example 2.

While this approach can be used to separate PEG conjugates having different molecular weights, this approach is generally ineffective for separating positional isomers having different pegylation sites within a protein. For example, gel filtration chromatography can be used to separate from each other mixtures of PEG 1-mers, 2-mers, 3-mers, etc., although each of the recovered PEG-mer compositions may contain PEGs attached to different reactive amino groups (e.g., lysine residues) within the protein.

Gel filtration columns suitable for carrying out this type of separation include Superdex™ and Sephadex™ columns available from Amersham Biosciences. Selection of a particular column will depend upon the desired fractionation range desired. Elution is generally carried out using a non-amine based buffer, such as phosphate, acetate, or the like. The collected fractions may be analysed by a number of different methods, for example, (i) OD at 280 nm for protein content, (ii) BSA protein analysis, (iii) iodine testing for PEG content (Sims G. E. C., et al., *Anal. Biochem*, 107, 60-63, 1980), or alternatively, (iv) by running an SDS PAGE gel, followed by staining with barium iodide.

Separation of positional isomers can be carried out by reverse phase chromatography using, for example, an RP-HPLC C18 column (Amersham Biosciences or Vydac) or by ion exchange chromatography using an ion exchange column, e.g., a Sepharose™ ion exchange column available from Amersham Biosciences. Either approach can be used to separate PEG-biomolecule isomers having the same molecular weight (positional isomers).

Depending upon the intended use for the resulting PEG-conjugates, following conjugation, and optionally additional separation steps, the conjugate mixture may be concentrated, sterile filtered, and stored at low temperatures from about −20° C. to about −80° C. Alternatively, the conjugate may be lyophilized, either with or without residual buffer and stored as a lyophilized powder. In some instances, it is preferable to exchange a buffer used for conjugation, such as sodium acetate, for a volatile buffer such as ammonium carbonate or ammonium acetate, that can be readily removed during lyophilization, so that the lyophilized protein conjugate powder formulation is absent residual buffer. Alternatively, a buffer exchange step may be used using a formulation buffer, so that the lyophilized conjugate is in a form suitable for reconstitution into a formulation buffer and ultimately for administration to a mammal.

Precursor Maleimide Polymer Derivatives and Polymer Succinamic Acid Conjugates

Precursor maleimide polymer derivatives useful in the present invention generally comprise at least one maleimide substituent coupled to a water soluble polymer segment. The maleimide substituent(s) can either be covalently bonded directly to a water soluble polymer segment, or alternatively can be connected to the polymer segment via a linking group, L. A generalized structure is provided as I below, where the optional linker is designated L, where $L_0$ indicates the absence of a linker, and $L_1$ indicates the presence of a linker.

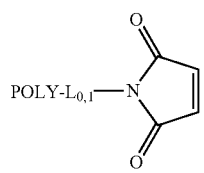

I

The corresponding polymer maleamic acid, II, and polymer succinamic acid conjugates, IV and V, have structures as provided below. Since the structures are all interrelated, the descriptions and embodiments provided herein for POLY and L apply equally to all of these structures.

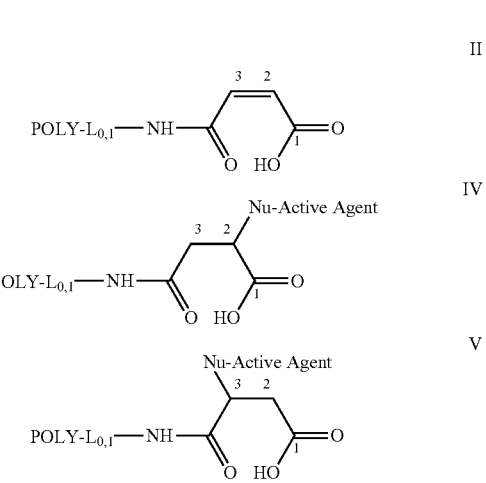

The Polymer Segment

As shown in the illustrative structures above, the polymer reagents and conjugates of the invention contain a water-soluble polymer segment. Representative POLYs include poly(alkylene glycols) such as poly(ethylene glycol), poly(propylene glycol) ("PPG"), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, and poly(N-acryloylmorpholine). POLY can be a homopolymer, an alternating copolymer, a random copolymer, a block copolymer, an alternating tripolymer, a random tripolymer, or a block tripolymer of any of the above. The water-soluble polymer segment is preferably, although not necessarily, a polyethylene glycol, "PEG", or a derivative thereof.

The polymer segment can have any of a number of different geometries, for example, POLY can be linear, branched, or forked. Most typically, POLY is linear or is branched, for example, having 2 polymer arms. Although much of the discussion herein is focused upon PEG as an illustrative POLY, the discussion and structures presented herein can be readily extended to encompass any of the water-soluble polymer segments described above.

Any water-soluble polymer having at least one reactive maleimide terminus can be used to prepare a polymer succinamic acid conjugate in accordance with the invention and the invention is not limited in this regard. Although water-soluble polymers bearing only a single reactive maleimide can be used, polymers bearing two, three, four, five, six, seven, eight, nine, ten, eleven, twelve or more reactive maleimides suitable for conversion to their open ring forms as set forth herein can be used. Nonlimiting examples of the upper limit of the number of maleimide or amino precursor moieties associated with the water-soluble polymer segment include from about 1 to about 500, from 1 to about 100, from about 1 to about 80, from about 1 to about 40, from about 1 to about 20, and from about 1 to about 10.

In turning now to the preferred POLY, PEG encompasses poly(ethylene glycol) in any of its linear, branched or multi-arm forms, including end-capped PEG, forked PEG, branched PEG, pendant PEG, and less preferably, PEG containing one or more degradable linkage separating the monomer subunits, to be more fully described below.

A PEG polymer segment comprises the following: $-(CH_2CH_2O)_n-CH_2CH_2-$, where (n) typically ranges from about 3 to about 4,000, or from about 3 to about 3,000, or more preferably from about 20 to about 1,000.

POLY can be end-capped, for example an end-capped PEG where PEG is terminally capped with an inert end-capping group. Preferred end-capped PEGs are those having as an end-capping moiety such as alkoxy, substituted alkoxy, alkenyloxy, substituted alkenyloxy, alkynyloxy, substituted alkynyloxy, aryloxy, substituted aryloxy. Preferred end-capping groups are methoxy, ethoxy, and benzyloxy. The end-capping group can also advantageously comprise a phospholipid. Exemplary phospholipids include phosphatidylcholines, such as dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin. In one embodiment, however, a polymer of the invention is substantially absent fatty acid groups or other lipophilic moieties.

Referring now to any of the structures containing a polymer segment, POLY, POLY may correspond or comprise the following:

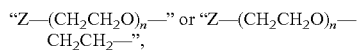

where n ranges from about 3 to about 4000, or from about 10 to about 4000, and Z is or includes a functional group, which may be a reactive group or an end-capping group. Examples of Z include hydroxy, amino, ester, carbonate, aldehyde, acetal, aldehyde hydrate, ketone, ketal, ketone hydrate, alkenyl, acrylate, methacrylate, acrylamide, sulfone, thiol, carboxylic acid, isocyanate, isothiocyanate, hydrazide, urea, maleimide, vinylsulfone, dithiopyridine, vinylpyridine, iodoacetamide, alkoxy, benzyloxy, silane, lipid, phospholipid, biotin, and fluorescein, including activated and protected forms thereof where applicable. Preferred are functional groups such as N-hydroxysuccinimidyl ester, benzotriazolyl carbonate, amine, vinylsulfone, maleimide, N-succinimidyl carbonate, hydrazide, succinimidyl propionate, succinimidyl butanoate, succinimidyl succinate, succinimidyl ester, glycidyl ether, oxycarbonylimidazole, p-nitrophenyl carbonate, aldehyde, orthopyridyl-disulfide, and acrylol.

These and other functional groups, Z, are described in the following references, all of which are incorporated by reference herein: N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670, 417), benzotriazole carbonate (see, e.g., U.S. Pat. No. 5,650, 234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acryloyl (see, e.g., Sawhney et al., Macromolecules, 26:581 (1993)), vinylsulfone (see, e.g., U.S. Pat. No. 5,900,461).

Again, the POLY structures shown immediately above may represent linear polymer segments, or may form part of a branched or forked polymer segment. In an instance where the polymer segment is branched, the POLY structures immediately above may, for example, correspond to the polymer arms forming part of the overall POLY structure. Alternatively, in an instance where POLY possesses a forked structure, the above POLY structure may, for example, correspond to the linear portion of the polymer segment prior to the branch point.

POLY may also correspond to a branched PEG molecule having 2 arms, 3 arms, 4 arms, 5 arms, 6 arms, 7 arms, 8 arms or more. Branched polymers used to prepare the polymer maleimides of the invention may possess anywhere from 2 to 300 or so reactive termini. Preferred are branched polymer segments having 2 or 3 polymer arms. An illustrative branched POLY, as described in U.S. Pat. No. 5,932,462, corresponds to the structure:

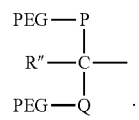

In this representation, R" is a nonreactive moiety, such as H, methyl or a PEG, and P and Q are nonreactive linkages. In a preferred embodiment, the branched PEG polymer segment is methoxy poly(ethylene glycol) disubstituted lysine, and corresponds to:

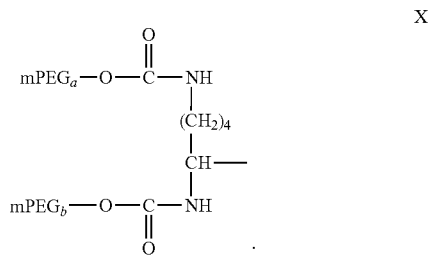

In the above particular branched configuration, the branched polymer segment possesses a single reactive site extending from the "C" branch point for positioning of the reactive maleimide group via a linker as described herein. Branched PEGs such as these for use in the present invention will typically have fewer than 4 PEG arms, and more preferably, will have 2 or 3 PEG arms. Such branched PEGs offer the advantage of having a single reactive site, coupled with a larger, more dense polymer cloud than their linear PEG counterparts.

One particular type of branched PEG maleimide corresponds to the structure: (MeO-PEG-)$_i$G-L$_{0,1}$-MAL, where MAL represents maleimide, i equals 2 or 3, and G is a lysine or other suitable amino acid residue.

An illustrative branched polymer maleimide of the invention has the structure shown below, where L is any of the herein described linkers.

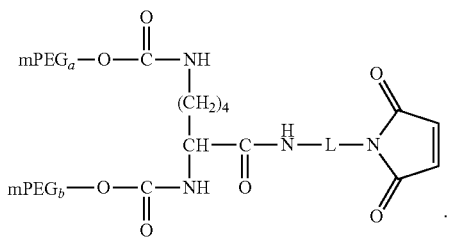

VI

An illustrative PEG maleimide having a branched structure as shown generally above corresponds to structure VII.

Branched PEGs for use in preparing a polymer maleimide of the invention additionally include those represented more generally by the formula $R(PEG)_n$, where R is a central or core molecule from which extends 2 or more PEG arms. The variable n represents the number of PEG arms, where each of the polymer arms can independently be end-capped or alternatively, possess a reactive functional group at its terminus, such as a maleimide or other reactive functional group. In such multi-armed embodiments of the invention, each PEG arm typically possesses a maleimide group at its terminus. Branched PEGs such as those represented generally by the formula, $R(PEG)_d$, above possess 2 polymer arms to about 300 polymer arms (i.e., n ranges from 2 to about 300). Branched PEGs such as these preferably possess from 2 to about 25 polymer arms, more preferably from 2 to about 20 polymer arms, and even more preferably from 2 to about 15 polymer arms or fewer. Most preferred are multi-armed polymers having 3, 4, 5, 6, 7 or 8 arms.

Preferred core molecules in branched PEGs as described above are polyols. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Preferred polyols include glycerol, pentaerythritol, sorbitol, and trimethylolpropane.

A representative multi-arm polymer structure of the type described above is:

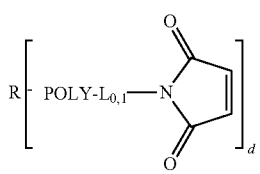

VII where d is an integer from 3 to about 100, and R is a residue of a central core molecule having 3 or more hydroxyl groups, amino groups, or combinations thereof.

Multi-armed PEGs for use in preparing a polymer maleimide of the invention include multi-arm PEGs available from Nektar, Huntsville, Ala. In a preferred embodiment, a multi-armed polymer maleimide of the invention corresponds to the following, where the specifics of the linkered maleimide portion of the molecule are provided elsewhere herein.

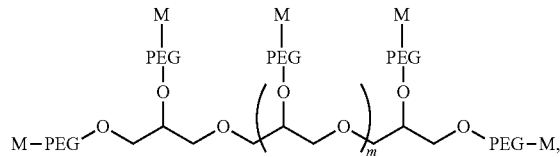

VII where
PEG is $-(CH_2CH_2O)_nCH_2CH_2-$,
M is:

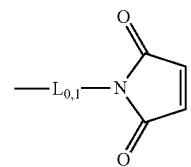

and m is selected from the group consisting of 3, 4, 5, 6, 7, and 8.

Alternatively, the polymer maleimide may possess an overall forked structure. An example of a forked PEG corresponds to the structure:

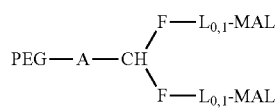

IX where PEG is any of the forms of PEG described herein, A is a linking group, preferably a hydrolytically stable linkage such as oxygen, sulfur, or $-C(O)-NH-$, F and F' are hydrolytically stable spacer groups that are optionally present, and the other variables, L and maleimide (MAL) are as defined above. Examplary linkers and spacer groups corresponding to A, F and F' are described in International Application No. PCT/US99/05333, and are useful in forming polymer segments of this type for use in the present invention. F and F' are spacer groups that may be the same of different. In one particular embodiment of the above, PEG is mPEG, A corresponds to $-C(O)-NH-$, and F and F' are both methylene or $-CH_2-$. This type of polymer segment is useful for reaction with two active agents, where the two active agents are positioned a precise or predetermined distance apart, depending upon the selection of F and F'.

An illustrative branched, forked PEG has the structure shown below, where the branched portion is on the left, and the forked portion having two maleimide groups extending therefrom in on the right.

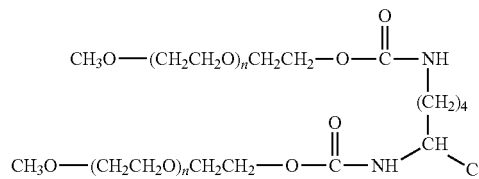
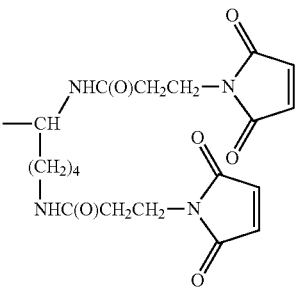

Alternatively, the PEG polymer segment for use in preparing a polymer maleimide of the invention may be a PEG molecule having pendant reactive groups along the length of the PEG chain rather than at the end(s), to yield a stabilized polymer maleimide having one or more pendant maleimide groups attached to the PEG chain by a linker, L.

Further, in a less preferred embodiment, the polymer segment itself may possess one or more weak or degradable linkages that are subject to hydrolysis. Illustrative degradable linkages that may be present in the polymer segment include but are not limited to carbonate, imine, phosphate ester, and hydrazone.

Generally, the nominal average molecular mass of the water-soluble polymer segment, POLY will vary. The nominal average molecular mass of POLY typically falls in one or more of the following ranges: about 100 daltons to about 100,000 daltons; from about 500 daltons to about 80,000 daltons; from about 1,000 daltons to about 50,000 daltons; from about 2,000 daltons to about 25,000 daltons; from about 5,000 daltons to about 20,000 daltons. Exemplary nominal average molecular masses for the water-soluble polymer segment POLY include about 1,000 daltons, about 5,000 daltons, about 10,000 daltons, about 15,000 daltons, about 20,000 daltons, about 25,000 daltons, about 30,000 daltons, and about 40,000 daltons. Low molecular weight POLYs possess molecular masses of about 250, 500, 750, 1000, 2000, or 5000 daltons.

Any of the above structures corresponding to a polymer-maleimide is meant to also encompass its corresponding polymer succinamic acid counterpart, even if not explicitly shown. Thus, all polymer maleimide structures herein are meant to extend to the same structure with the exception that the maleimide ring is in its open-ring form, and can be unconjugated (maleamic acid) or conjugated (succinamic acid conjugate).

The Linker

In turning now to the linker moiety, a linker moiety or simply "linker" of the invention is represented generally by the variable, L. A linker of the invention, L, if present, typically contains from about 1 to about 40 atoms. The linker is the portion of the overall polymer that links the maleimide or maleamic acid or succinamic acid portion of the polymer with the polymer segment. A linker of the invention may be a single atom, such as an oxygen or a sulfur, two atoms, or a number of atoms. A linker is typically but is not necessarily linear in nature. The overall length of the linker will typically range between 1 to about 40 atoms, where by length is meant the number of atoms in a single chain, not counting substituents. For instance, —$CH_2$— counts as one atom with respect to overall linker length, —$CH_2CH_2O$— counts as 3 atoms in length. Preferably, a linker will have a length of about 1 to about 20 atoms, or from about 2 to about 15 atoms, or from about 1 to about 6 atoms, and is hydrolytically stable.

A linker of the invention can be a single functional group such as an amide, an ester, a urethane, or a urea, or may contain methylene or other alkylene groups flanking either side of the single functional group. Alternatively, a linker may contain a combination of functional groups that can be the same or different. Additionally, a linker of the invention can be an alkylene chain, optionally containing one or more oxygen or sulfur atoms (i.e., an ether or thioether). Preferred linkers are those that are hydrolytically stable. When viewed in the context of the structures herein, a linker is one that when considered as part of the overall polymer, does not result in an overall structure containing a peroxide bond (—O—O—) or an —N—O— or —O—N— bond.

In the context of structures I, II, a linker of the invention may be any of the following: —O—, —NH—, —S—, —C(O)—, C(O)—NH, NH—C(O)—NH, O—C(O)—NH, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—$CH_2$—$CH_2$—O—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—$CH_2$—C(O)—NH—, C(O)—NH—$CH_2$—$CH_2$—, —$CH_2$—$CH_2$—$CH_2$—$CH_2$—, C(O)—NH—, —C(O)—O—$CH_2$—, —$CH_2$—C(O)—O—$CH_2$—, —$CH_2$—$CH_2$—C(O)—O—$CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$, —$CH_2$—$CH_2$—NH—C(O)—$CH_2$—$CH_2$, —C(O)—NH—$CH_2$—, —C(O)—NH—$CH_2$—$CH_2$—, —O—C(O)—NH—$CH_2$—, —O—C(O)—NH—$CH_2$—

$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—C(O)—, —$CH_2$—$CH_2$—$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—$CH_2$—, bivalent cycloalkylene group, —N($R^6$)—, —$CH_2$—$CH_2$—$CH_2$—C(O)—NH—$CH_2$—$CH_2$—NH—C(O)—$CH_2$—$CH_2$—, —O—C(O)—NH—$[CH_2]_h$—($OCH_2CH_2)_j$—, and combinations of two or more of any of the foregoing, wherein (h) is 0 to 6, (j) is 0 to 20, $R^6$ is H or an organic radical selected from the group consisting of alkyl, substituted alkyl, alkenyl, substituted alkenyl, alkynyl, substituted alkynyl, aryl and substituted aryl.

For purposes of the present disclosure, however, a series of atoms is not considered as a linker moiety when the series of atoms is immediately adjacent to a polymer segment, POLY, and the series of atoms is but another monomer such that the proposed linker moiety would represent a mere extension of the polymer chain. For example, given the partial structure "POLY-L-," where POLY in this instance is defined as "$CH_3O(CH_2CH_2O)_n$—", the linker moiety would not be "—$CH_2CH_2O$—" since such a definition would merely represent an extension of the polymer. That is not to say, however, that a linker of the invention cannot possess one or more contiguous —$CH_2CH_2O$— portions. For example, a linker may contain one or more (—$CH_2CH_2O$—) subunits flanked on one or both sides by one or a combination of illustrative linkers as provided above.

In one embodiment of the invention, a linker possesses the structure:

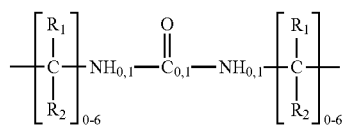

In the above linker, $R^1$ and $R^2$ in each occurrence are each independently H or an organic radical that is selected from the group consisting of alkyl, substituted alkyl, cycloalkyl, substituted cycloalkyl, alkylenecycloalkyl, and substituted alkylenecycloalkyl. In the above structure, a subscript of zero indicates the absence of that particular atom or functional group.

Using a single maleimide end group and a methoxy cap as a representation, certain exemplary PEG maleimide structures are illustrated in Structures 1-4 below. The linkers, L, shown in Table 1, may be used to form the maleamic acid polymers and conjugates of the invention. The PEG maleimide represented by Structure 3-ET is called "linkerless" since the maleimide ring simply replaces the terminal hydroxyl group in the PEG. The exemplary linkers shown below can be utilized in combination with any of the above described polymer segments; the embodiments below with mPEG are meant only to be illustrative.

TABLE 1

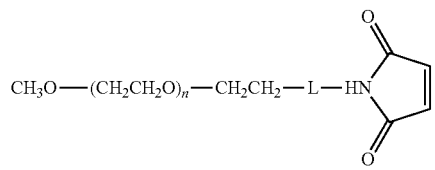

$L_1 =$ —NH—C(O)—X—

| Linker Abbrev. | X |
|---|---|
| AMET | —$(CH_2)_2$— |
| AMTR | —$(CH_2)_3$— |
| AMPE | —$(CH_2)_5$— |
| MCH | —cyclohexyl-$CH_2$— |
| TEO | —(O—$CH_2CH_2$)—C(O)—NH—$CH_2CH_3$ |
| mPH | meta-phenylene-$CH_3$ |
| pPHAL | para-phenylene-$CH_2CH_2$— |

$L_2 =$ —NH—Y—

| Linker Abbrev. | Y |
|---|---|
| BU | —$(CH_2)_4$— |
| HE | —$(CH_2)_6$— |

$L_3 =$ —O—Z—

| Linker Abbrev. | Z |
|---|---|
| ET | —$(CH_2)_2$— |
| PR | —$(CH_2)_3$— |
| PRAC | —C(O)—$CH_2CH_2$— |

$L_4 =$ —$CH_2$—Q

| Linker Abbrev. | Q |
|---|---|
| PACA | —C(O)— |
| PAME | —C(O)—NH—$CH_2$— |
| PAET | —C(O)—NH—$CH_2CH_2$— |
| BAET | —$(CH_2)$—C(O)NH—$CH_2CH_2$— |
| PAHE | —C(O)—NH—$(CH_2)_6$— |
| BAET | —$CH_2$—C(O)NH—$(CH_2)_6$— |
| PAOX | —C(O)—NH—$CH_2CH_2O$— |

Generally, preferred are linkers that are effective to provide a rate of ring opening hydrolysis of the uncoupled polymer maleimide that is increased (i.e., faster) than that of the same water soluble polymer maleimide absent a linker. In a preferred embodiment, the linking group facilitates ring opening such that the ring opening hydrolysis rate of the maleimide has a half life equal to or shorter than about 12 hours at pH 7.5 when measured at room temperature. In a more preferred embodiment, the linking group facilitates ring opening such that the ring opening hydrolysis rate of the maleimide has a half life equal to or shorter than about 12 hours at pH 9 when measured at room temperature. Preferred linking groups that facilitate ring opening include the linkerless maleimides, i.e. $L_3$-ET, those with short alkyl linkers, e.g. $L_3$-PR, those with an ethylene or aryl group attached to the maleimide ring nitrogen, e.g. $L_1$-MCH and $L_1$-pPHAL, those with short alkyl linkers between the maleimide nitrogen atom and a carbonyl group, e.g. $L_1$-AMET and various modifications of the listed groups that contain substituents that enhance electron withdrawal from the maleimide ring nitrogen without providing significant steric hindrance to hydrolysis, i.e. no branching substitution to the linker atom attached to the ring nitrogen. Preferred linkers possess an electron withdrawing group within about 6 atoms of the maleimide or maleimide-derived nitrogen, i.e., within 1, 2, 3, 4, 5, or 6 atoms of the maleimide or maleimide derived nitrogen, or even more preferably, within about 3 atoms.

Polymers and conjugates of the invention include mono-functional, bifunctional, and multi-functional structures as previously described.

For instance, a polymer maleimide precursor of a polymer or conjugate of the invention may be described generally by the following structure where the variables are as defined elsewhere herein:

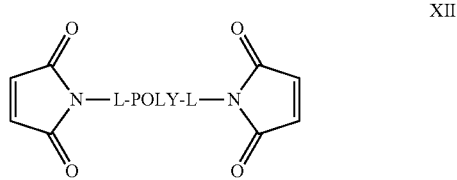

XII

In the above embodiment, the L's may be the same of different. In one particular embodiment the polymer reagent is homo-bifunctional, that is to say, both L's are the same.

Succinamic Acid Conjugates

The generalized features of the conjugates of the invention have been described in detailed fashion above. Active agents that are covalently attached to a polymer succinamic acid encompass any of a number of types of molecules, entities, surfaces, and the like, as will become apparent from the following.

Target Molecules and Surfaces

The polymer maleimides (both open and closed ring) of the invention may be attached, either covalently or non-covalently, to a number of entities including films, chemical separation and purification surfaces, solid supports, metal/metal oxide surfaces such as gold, titanium, tantalum, niobium, aluminum, steel, and their oxides, silicon oxide, macromolecules, and small molecules. Additionally, the polymers and methods of the invention may also be used in biochemical sensors, bioelectronic switches, and gates. The polymers and methods of the invention may also be employed in preparing carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

A biologically active agent for use in providing a conjugate of the invention may be any one or more of the following. Suitable agents may be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, antibodies, polysaccharides, steroids, nucleotides, oligonucleotides, polynucleotides, fats, electrolytes, and the like. Preferably, an active agent for coupling to a polymer maleimide possesses a native amino or a sulfydryl group, or alternatively, is modified to contain at least one reactive amino or sulfhydryl group suitable for coupling to a polymer maleimide.

Specific examples of active agents suitable for covalent attachment to a polymer of the invention include but are not limited to aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin).

Additional agents suitable for covalent attachment to a polymer include but are not limited to amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Preferred peptides or proteins for coupling to a polymer maleimide of the invention include EPO, IFN-α, IFN-β, IFN-γ, consensus IFN, Factor VII, Factor VIII, Factor IX, IL-2, remicade (infliximab), Rituxan (rituximab), Enbrel (etanercept), Synagis (palivizumab), Reopro (abciximab), Herceptin (trastuzimab), tPA, Cerizyme (imiglucerase), Hepatitus-B vaccine, rDNAse, alpha-1 proteinase inhibitor, GCSF, GMCSF, hGH, insulin, FSH, and PTH.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. The above biologically active proteins are additionally meant to encompass variants having one or more amino acids substituted (e.g., cysteine), deleted, or the like, as long as the resulting variant protein possesses at least a certain degree of activity of the parent (native) protein.

The conjugates or methods described herein can also be extended to hydrogel formulations.

Pharmaceutical Compositions

The present invention also includes pharmaceutical preparations comprising a conjugate as provided herein in combination with a pharmaceutical excipient. Generally, the conjugate itself will be in a solid form (e.g., a precipitate) or in solution, which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

Methods of Administering

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that individual water-soluble polymer portions can be cleaved off. Such a result is advantageous when clearance from the body is potentially a problem because of the polymer size. Optimally, cleavage of each water-soluble polymer portion is facilitated through the use of physiologically cleavable and/or enzymatically degradable linkages such as urethane, amide, carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

All articles, books, patents, patent publications and other publications referenced herein are incorporated by reference in their entireties.

EXAMPLES

It is to be understood that while the invention has been described in conjunction with certain preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains.

Abbreviations.
DCM: dichloromethane
NMR: nuclear magnetic resonance
DI: deionized
r.t. room temperature
anh. anhydrous
Da Daltons
GPC Gel Permeation Chromatography
Materials and Methods.

All chemical reagents referred to in the appended examples are commercially available unless otherwise indicated.

All PEG reagents referred to in the appended examples are available from Nektar, Huntsville, Ala. All $^1$HNMR data was generated by a 300 or 400 MHz NMR spectrometer manufactured by Bruker.

Example 1

Hydrolysis Rates of Exemplary Linkered PEG Maleimides

A series of representative methoxy-PEG maleimides with an average molecular weight of 5000 Daltons was synthesized and studied. The kinetics of the hydrolysis reaction of the maleimide ring for each structure below was determined by measuring the UV absorption at 297 nm of solutions of each mPEG maleimide at a concentration of 5 mg/mL in 50 mM Phosphate Buffer at pH of approximately 7.5.

The generalized structure for the polymer maleimides is shown below. Exact structures corresponding to each of the linkers ($L_1$, $L_2$, and $L_3$) is provided in Table 1 above.

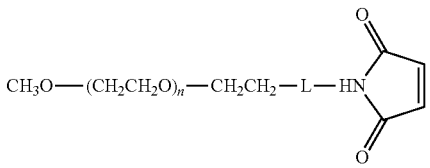

TABLE 2

Hydrolysis Rates of mPEG (5 k-Da) Maleimides (5 mg/mL) in 50 mM Phosphate Buffer (pH ~7.5) as Measured by UV Absorption at 297 nm

| Structure | half-life (hrs) | Relative Rate |
|---|---|---|
| $L_1$-AMTR | 8.8 | 3.66 |
| $L_1$-AMPE | 19.4 | 1.66 |
| $L_1$-MCH | 16.3 | 1.98 |
| $L_2$-BU | 19.6 | 1.65 |
| $L_2$-HE | 32.3 | 1.00 |
| $L_3$-ET | 8.1 | 4.01 |
| $L_3$-PR | 11.5 | 2.82 |

As shown by the data in Table 2, the hydrolysis rates of the illustrative polymer maleimides vary with structure. In this group, the HE linker is the most resistant to hydrolysis, while the ET linker exhibits the fastest hydrolysis rate, indicating the tendency of its maleimide ring towards hydrolysis, even at fairly mild pHs.

The data above indicates that preferred linking groups for facilitating ring opening include those having a strong electron-withdrawing group, EWG, in close proximity (most preferably within 3 or so atoms) to the maleimide substituent (s), i.e., the nitrogen of the maleimide ring. The $L_3$-ET linker, —O-ethylene-, possesses an electron withdrawing atom, oxygen, within 3 atoms of the maleimide nitrogen, which appears to contribute to its tendency towards an enhanced rate of hydrolysis. Preferred are linkers having an EWG most preferably within 1, 2, 3 or 4 atoms of the maleimide nitrogen.

Example 2

Hydrolysis of a Branched and Linkered Polymer Maleimide, mPEG2-MAL-40K

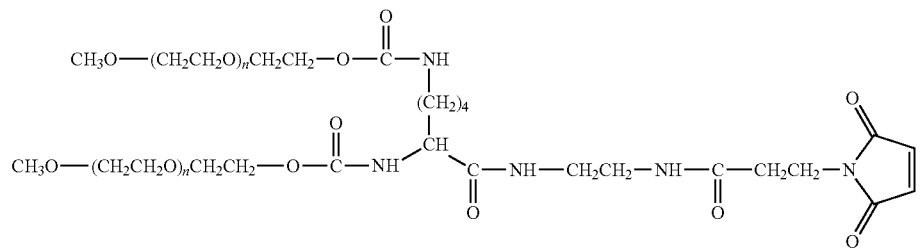

The polymer maleimide pictured above, mPEG2-MAL-40K, was obtained from Nektar (Huntsville, Ala.). This polymer derivative undergoes a limited degree of hydrolysis of the maleimide ring under certain conditions to form the corresponding maleamic acid derivative, as described below.

Figure 3:
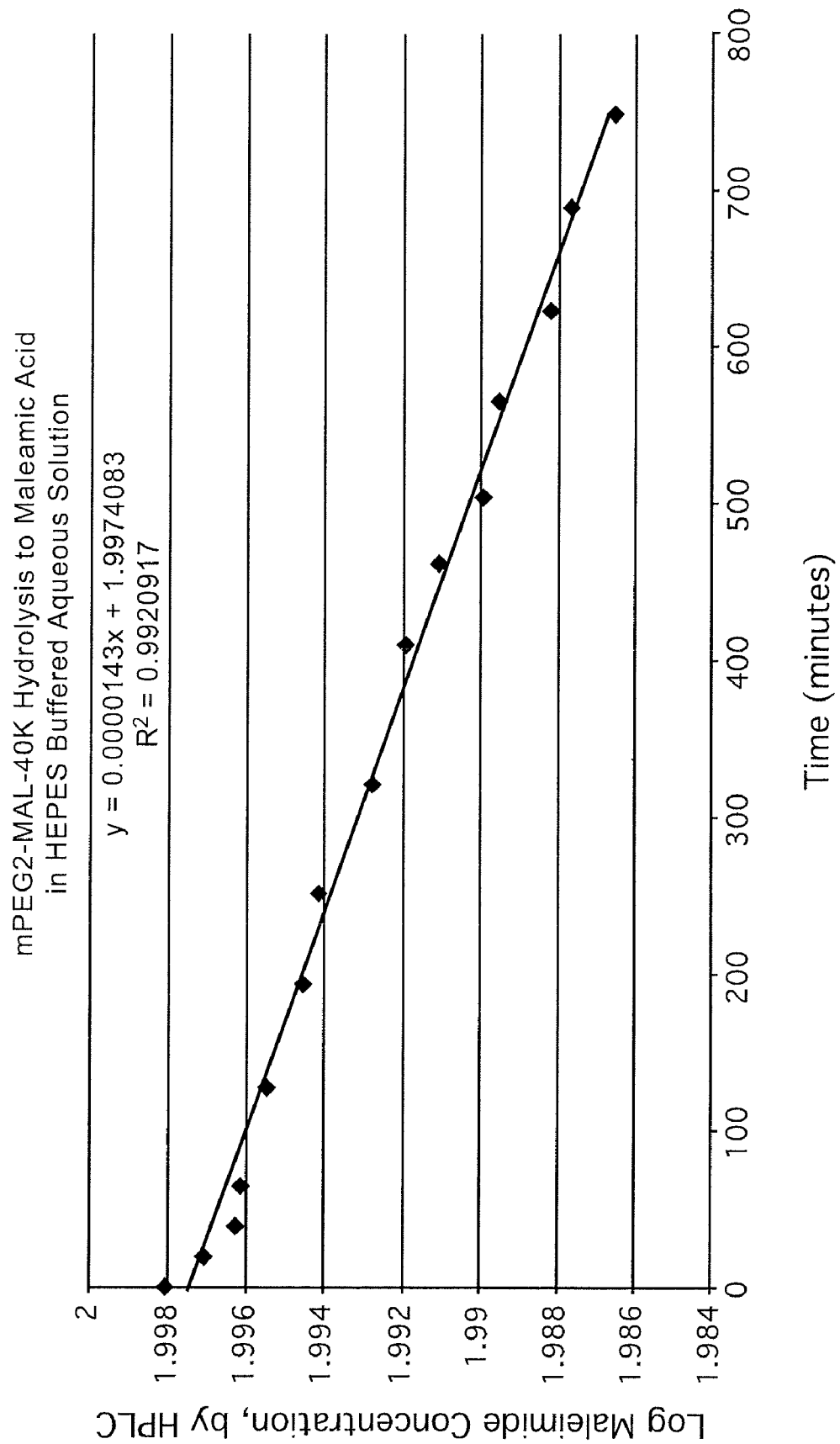
FIG. 3 is a plot of the logarithm of the concentration of an illustrative branched polymer linkered maleimide over time as described in detail in Example 2.

The hydrolysis reaction was monitored analytically by observing the percentage decrease of the parent maleimide over time by HPLC. The kinetics of the hydrolysis reaction was determined at a pH of about 5.5, using a HEPES buffered solution at approximately 25° C. A linear correlation was obtained from the raw data by plotting either the logarithm of the concentration of either the maleamic acid or the maleimide versus time (the latter is shown in FIG. 3).

That data was then used to determine the half-life of the hydrolysis reaction, which was calculated to be approximately 34 days under the conditions examined. Thus, under these conditions, this particular maleimide is resistant to ring opening. However, in unbuffered water, again at 25° C. and at a higher pH, the hydrolysis of mPEG2-MAL-40K was determined to have a half-life of about 2.1 days, when measured in the same way.

Example 3

Hydrolysis Rate Study of Polymer succinimide Conjugates

The hydrolysis rates of representative protein and small molecule model conjugates were investigated to examine the correlation between the ring opening tendencies of the polymer-terminated maleimides themselves versus their conjugates.

Since large biomolecular components such as proteins have a dramatic effect on the retention of conjugated molecules on common liquid chromatography columns, it is generally more difficult to measure kinetics of maleimide conjugates than it is for the polymers themselves. In this analysis, the open acid form of the maleamic acid was not distinctly separable from the unopened or closed ring form. However, a combination analysis based upon size exclusion chromatography (HPLC-SE) and analytical protein electrophoresis (SDS-PAGE) was successfully employed to estimate the ring opening characteristics of polymeric maleimide protein conjugates, as well as conjugates prepared using model non-protein compounds.

In this study, two PEG-globular protein conjugates represented generally below were studied to examine their ring opening characteristics.

The top structure is a PEG-maleimide conjugate of Glob Protein 2, where Glob Protein 2 is a protein having a molecular weight of approximately 48 kDa. Glob Protein 2 was conjugated to a PEG maleimide derived from a PEG propionic acid, MW 30 kDa, which further included a medium-length linker interposed between the propionic acid derived portion of the polymer and the maleimide terminus. The linker in the top structure is $-C(O)-NH(CH_2)_2-NH-C(O)-CH_2CH_2-$.

The bottom structure is a PEG-maleimide conjugate of Glob Protein 1, where the protein possesses a molecular weight of about 11 kDa. The conjugate was prepared using a linkerless maleimide (mPEG-MAL) having a molecular weight of about 20 kDa. The corresponding PEG maleimide structure is 3-ET.

The bottom structure (Glob Protein 2) is completely ring opened after 24 hours at pH 8.5 at room temperature, thus indicating the instability of this type of maleimidyl terminated polymer. Thus, this polymer conjugate is a good candidate for promoting the ring-opening reaction to provide a chemically stable composition, that is to say, one at equilibrium, that comprises the polymer succinamic acid conjugate. Relative to the linkerless form, however, the linker in the top structure (Glob Protein 1) appears to retard the ring opening, since the ring structure in the top conjugate is not completely ring-opened until 17 hours, at pH 9, upon heating to 50° C. for 17 hours.

Example 4

Ring Opening Characteristics of Model PEG-Succinimide Conjugates

The hydrolysis rates of certain illustrative polymer maleimides conjugated to a model compound, 2-mercaptoethanol, were determined to assess the tendency of the conjugates towards ring-opening, and thus their suitability for the ring-opening approach provided herein.

Hydrolysis rate studies of conjugates having the structures shown below, where the linkers include portions designated as TRI, PEN, and MCH, were conducted as described above for the unconjugated maleimides. The half-lives shown were calculated from data taken at two different pH values. Similar

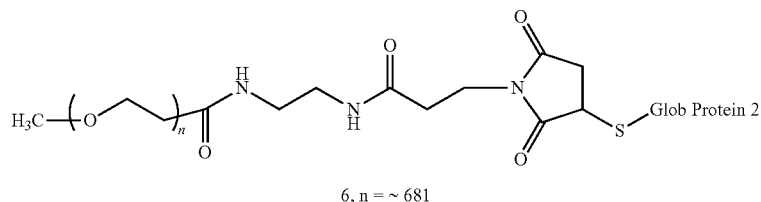

6, n = ~ 681

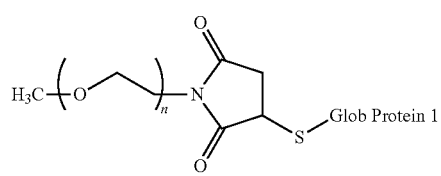

7, n = ~ 452 to the unconjugated maleimides, the data indicate a slowing in reaction rate as the pHs drifted lower with increased ring opening. The linkage with the shortest hydrocarbon chain adjacent to the succinimide ring (i.e., TRI) was the fastest to open in comparison to the other conjugates studied.

TABLE 3

Hydrolysis Half-lives of mPEG (5 k-Da) Maleimide Conjugates

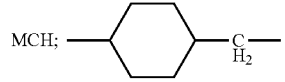

| Linker, D | Experimentally Determined Half-lives | |
|---|---|---|
| | pH 9.06 | pH 8.11 |
| TRI; trimethylene | 31.4 hours | 17.6 days |
| PEN; pentamethylene | — | 28.5 days |
| MCH; | 43.3 hours | — |

Example 5

Hydrolysis at Various PH Values for a Linkerless MPEG-Maleimikde

Hydrolysis studies of conjugates formed by reaction of the model compound, 2-mercaptoethanol, with mPEG-5K-Maleimide were carried out as described previously. A summary of the kinetics of the hydrolysis reaction of the conjugates at various pHs is provided in Table 4 below.

TABLE 4

HYDROLYSIS STUDY OF AN ADDUCT OF M-PEG(5K)-MAL WITH 2-MERCAPTOETHANOL

| pH | Half-life, min |
|---|---|
| 12 | <5 |
| 11 | <15 |
| 10 | 30 |
| 9 | 600 |

Synthesis of an mPEG-5K-Maleimide Adduct with 2-Mercaptoethanol (mPEG-MAL-ME).

To a solution of mPEG(5000 Da)-maleimide (3.0 g, 0.0006 moles, Nektar, Huntsville, Ala.) in acetonitrile (60 ml), 2-mercaptoethanol (0.15 g, 0.0190 moles) was added and the mixture was stirred overnight at room temperature under an argon atmosphere. The solvents were then distilled off under reduced pressure. The residue was dissolved in dichloromethane (7.5 ml) and isopropyl alcohol was then added. The precipitated product was filtered off and dried under reduced pressure. Yield: 2.80 g.

NMR (d6-DMSO): 2.78 ppm (bm, —S—CH$_2$CH$_2$OH, 2H), 3.24 ppm (s, —OCH$_3$, 3H), 3.51 ppm (s, PEG segment), 4.03 ppm (m, —CH—S—, 1H), 4.85 ppm (7, —OH, 1H).

Hydrolysis at pH 9 mPEG-MAL-ME (0.2 g) was dissolved in 4 ml of distilled water and the resulting solution was added to 4 ml of 0.1 M phosphate buffer (pH=9.3). The pH was adjusted immediately to 9.0 by addition of 0.01M NaOH. 0.25 ml samples of the solution were withdrawn at 1 h intervals and analyzed by HPLC. During measurement the pH of the solution was maintained within a range of 8.95-9.05 by periodic addition of 0.01M NaOH.

Isolation of Succinamic Acid Conjugates

Carrying out the hydrolysis reaction as described above, the products were isolated from reactions conducted at pH 9 and pH 12. In each case the products were the same. Two products of hydrolysis were formed, the corresponding 2-position adduct and the 3-position adduct. Product assignments were made on the basis of spectral simulations. NMR analysis revealed that the molar ratio of the 2-position adduct to the 3-position adduct was 71 to 29.

Many modifications and other embodiments of the invention will come to mind to one skilled in the art to which this invention pertains having the benefit of teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method comprising administering a composition to an individual, wherein the composition comprises a plurality of conjugates, each conjugate in the plurality a protein derivatized with a water-soluble polymer, wherein the polymer is coupled to the protein via succinimide groups covalently attached to either cysteine sulfhydryl groups or lysine amino groups, and substantially all of the succinimide groups present in the composition are present in a ring-opened form.

2. The method of claim 1, wherein 95% or greater of all the succinimide groups present in the composition are present in a ring-opened form.

3. The method of claim 1, wherein the polymer is coupled to the protein via succinimide groups covalently attached to cysteine sulfhydryl groups.

4. The method of claim 3, wherein 95% or greater of all the succinimide groups present in the composition are present in a ring-opened form.

5. The method of claim 1, wherein the polymer is coupled to the protein via succinimide groups covalently attached to lysine amino groups.

6. The method of claim 5, wherein 95% or greater of all the succinimide groups present in the composition are present in a ring-opened form.

7. The method of claim 1, wherein the water-soluble polymer is selected from the group consisting of a poly(alkylene oxide), poly(vinyl pyrrolidone), poly(vinyl alcohol), polyoxazoline, poly(acryloylmorpholine), and poly(oxyethylated polyol).

8. The method of claim 7, wherein the water-soluble polymer is a poly(alkylene oxide).

9. The method of claim 8, wherein the water-soluble polymer is a poly(ethylene glycol).

10. The method of claim 9, wherein said poly(ethylene glycol) comprises an end-capping moiety.

11. The method of claim 10, wherein said end-capping moiety is selected from the group consisting alkoxy, substituted alkoxy, alkenyloxy, substituted alkenyloxy, alkynyloxy, substituted alkynyloxy, aryloxy, and substituted aryloxy.

12. The method of claim 11, wherein said end-capping moiety is selected from the group consisting of methoxy, ethoxy, and benzyloxy.

13. The method of claim 9, wherein said poly(ethylene glycol) has a nominal average molecular mass of from about 100 daltons to about 100,000 daltons.

14. The method of claim 13, wherein said poly(ethylene glycol) has a nominal average molecular mass of from about 1,000 daltons to about 80,000 daltons.

15. The method of claim 14, wherein said poly(ethylene glycol) has a nominal average molecular mass of from about 2,000 daltons to about 50,000 daltons.

16. The method of claim 9, wherein said poly(ethylene glycol) has a structure selected from the group consisting of linear, branched, forked, and multi-armed.

17. The method of claim 1, wherein said water-soluble polymer comprises a linker, L, interposed between said water-soluble polymer and said maleimide group.

18. The method of claim 9, wherein said poly(ethylene glycol) is directly attached to the nitrogen atom of said maleimide group.

* * * * *